US011324949B2

(12) United States Patent
Jomehri et al.

(10) Patent No.: US 11,324,949 B2
(45) Date of Patent: May 10, 2022

(54) SYSTEMS AND METHODS FOR ELECTRICAL MUSCLE STIMULATION

(71) Applicant: Eleway Industries Inc., North York (CA)

(72) Inventors: Amir Jomehri, North York (CA); Jeffrey Burton, Toronto (CA); Chengkai Yao, Scarborough (CA)

(73) Assignee: Eleway Industries Inc., North York (CA)

(*) Notice: Subject to any disclaimer, the term of this patent is extended or adjusted under 35 U.S.C. 154(b) by 577 days.

(21) Appl. No.: 16/622,717

(22) PCT Filed: Jun. 15, 2017

(86) PCT No.: PCT/CA2017/050735
§ 371 (c)(1),
(2) Date: Dec. 13, 2019

(87) PCT Pub. No.: WO2017/214731
PCT Pub. Date: Dec. 21, 2017

(65) Prior Publication Data
US 2020/0246614 A1    Aug. 6, 2020

Related U.S. Application Data

(60) Provisional application No. 62/414,651, filed on Oct. 28, 2016, provisional application No. 62/350,367, filed on Jun. 15, 2016.

(51) Int. Cl.
*A61N 1/36* (2006.01)

(52) U.S. Cl.
CPC ..... *A61N 1/36003* (2013.01); *A61N 1/36031* (2017.08)

(58) Field of Classification Search
CPC ... A61N 1/36003; A61N 1/36031; A61N 1/36
(Continued)

(56) References Cited

U.S. PATENT DOCUMENTS

| 4,712,558 A | 12/1987 | Kidd et al. |
| 5,350,415 A | 9/1994 | Cywinski |
| 2005/0283204 A1* | 12/2005 | Buhlmann ........... A61B 5/4836 607/48 |

(Continued)

OTHER PUBLICATIONS

Written Opinion of the International Searching Authority for PCT/CA2017/050735.

*Primary Examiner* — Amanda K Hulbert
*Assistant Examiner* — Philip C Edwards
(74) *Attorney, Agent, or Firm* — Kevin Shipley; Fogler, Rubinoff LLP

(57) ABSTRACT

A system for electrically stimulating one or more muscle groups includes a processor-readable storage medium storing, in association with each of at least one muscle group, digital exertion data representative of one or more action potentials captured during an exertion regime from the muscle group of a respective subject; a signal generator for generating electrical stimulation signals; processing structure configured to automatically retrieve digital exertion data from the processor-readable storage medium and to automatically cause the signal generator to generate new electrical stimulation signals based on the digital exertion data; and a signal distributor for conveying the new electrical stimulation signals from the signal generator to one or more respective muscle groups of at least one different subject. Also provided is a system for providing exercise session data including a capture subsystem capturing one or more action potentials from at least one muscle group of a subject during an exertion regime, the capture subsystem including a processor-readable storage medium; processing structure generating digital exertion data representative of the one or more action potentials and creating the exercise session data (Continued)

by: storing the digital exertion data in association with an identification of the respective muscle group in the processor-readable storage medium; storing, in the processor-readable storage medium, one or more exercises each defining at least the digital exertion data for one or more muscle groups; and storing, in the processor-readable storage medium, one or more sessions each defining at least one or more of the exercises, a publishing subsystem for publishing the exercise session data for download and use by at least one different subject to cause another processing structure to generate and distribute new electrical stimulation signals to one or more respective muscle groups of the at least one different subject. Related methods are disclosed.

17 Claims, 8 Drawing Sheets

(58) Field of Classification Search
USPC .......................................................... 607/46
See application file for complete search history.

(56) References Cited

U.S. PATENT DOCUMENTS

| | | | |
|---|---|---|---|
| 2005/0283205 A1* | 12/2005 | Lee | A61B 5/389 |
| | | | 607/48 |
| 2008/0027507 A1* | 1/2008 | Bijelic | A61N 1/0452 |
| | | | 607/48 |

* cited by examiner

| Stimulation ID | Stimulation Name | Exertion Data | Output Path |
|---|---|---|---|
| Stim1 | Delt | ～⌒～ | Lead A, Lead B |
| Stim2 | Shoulder Back | ⌒⌒⌒⌒ | Lead C, Lead D |
| Stim3 | Shoulder Mid | ～⌒～ | Lead E, Lead F |
| Stim4 | Shoulder Front | ⌒⌒⌒ | Lead G, Lead H |
| Stim5 | Lower Back | ～⌒～ | Lead I, Lead J |
| Stim6 | Pecs | ⌒⌒⌒ | Lead K, Lead L |
| Stim7 | Side Chest | ⋏⋏⋏⋏⋏ | Lead M, Lead N |
| Stim8 | Side Abs | ⋏⋏⋏⋏⋏ | Lead O, Lead P |
| Stim9 | Upper Front Abs | ～⌒～ | Lead Q, Lead R |
| Stim10 | Lower Front Abs | ⋏⋏⋏⋏⋏ | Lead S, Lead T |
| ... | ... | ... | ... |

Figure 8

SYSTEMS AND METHODS FOR ELECTRICAL MUSCLE STIMULATION

CROSS-REFERENCE TO RELATED APPLICATIONS

This application claims the benefit of U.S. Provisional Patent Application Ser. No. 62/350,367 filed on Jun. 15, 2016 and of U.S. Provisional Patent Application Ser. No. 62/414,651 filed on Oct. 28, 2016, the contents of each of which are incorporated herein by reference.

FIELD OF THE INVENTION

This application relates generally to electrical muscle stimulation, and more particularly to systems and methods for electrical muscle stimulation.

BACKGROUND OF THE INVENTION

Electrical muscle stimulation (EMS) has been widely accepted as a form of muscle conditioning and stimulation. Many high-level, FDA-approved EMS projects have been launched to exploit the benefits of EMS. EMS in physiotherapy rehab, as well as products and services for conditioning including those provided by EMS Fitness Canada (http://www.emsfitness.ca), have become available. In the consumer-level space, the likes of Dr. Ho's muscle therapy device is available but is not considered definitively to be a high-level FDA-approved device.

During traditional exercise, when muscles contract and spend time under tension, small microfiber tears start to elicit themselves on the myofibril line which the body repairs in order to become stronger.

In order to build muscle, the muscle needs to do 'work'. Work can only be done if there is movement. Muscle is most efficiently built when a focus is placed on "time under tension." It is generally felt that time under tension is easier to maintain when muscles are stimulated using EMS than when stimulated with conventional weights.

Weight training including muscle building is known to have a significant effect on hormonal balance and the overall health of the human body, and a healthy person will always have a better chance of fighting off dangerous diseases. However, if a person is unhealthy, he or she is often not motivated, or is often not even able, to undertake weight training to put themselves into a healthier condition. Because EMS can make time under tension easier to maintain, it is being considered as a replacement to weights for resistance training in both healthy athletes and relatively unhealthy patients.

Products available for applying EMS tend to create electrical stimulation signals based on standard waveforms that are artificially created for general purpose use. Using electrical leads, such general electrical stimulation signals tend to be applied in the same way to disparate muscle groups of a subject as needed. While the maximum amplitudes of the standard signals can be controlled, there is little consideration paid to the differences between the nature of an electrical stimulation signal that, for example, would best stimulate a quadricep muscle group and the nature of an electrical stimulation signal that would best stimulate a rear delt muscle group.

While existing EMS systems are useful, improvements are desirable.

SUMMARY OF THE INVENTION

In accordance with an aspect of the invention, there is provided a system for electrically stimulating one or more muscle groups comprising a processor-readable storage medium storing, in association with each of at least one muscle group, digital exertion data representative of one or more action potentials captured during an exertion regime from the muscle group of a respective subject; a signal generator for generating electrical stimulation signals; processing structure configured to automatically retrieve digital exertion data from the processor-readable storage medium and to cause the signal generator to generate new electrical stimulation signals based on the digital exertion data; and a signal distributor for conveying the new electrical stimulation signals from the signal generator to one or more respective muscle groups of at least one different subject.

Because the new electrical stimulation signals are based on digital exertion data representative of action potentials captured during an exertion regime from the corresponding muscle group of a subject, they can potentially be more effective at sustaining time under tension in a way that is appropriate for that muscle group but may not be as appropriate for another muscle group. Furthermore, automatic retrieval of exertion data and generation of corresponding new electrical stimulation signals based on the digital exertion data enables a user to receive effective muscle stimulation without requiring the supervision or control over the process by professional trainer or clinician.

In an embodiment, the processing structure is configured to retrieve the digital exertion data from the processor-readable storage medium as one or more exercises each defining the digital exertion data for one or more muscle groups.

In an embodiment, the processing structure is configured, in the event that an exercise defines digital exertion data for two or more muscle groups, to cause simultaneous distribution of new electrical stimulation signals based on the digital exertion data for the two or more muscle groups.

In an embodiment, the processing structure is configured to retrieve the digital exertion data from the processor-readable storage medium as one or more sessions each defining one or more of the exercises.

In an embodiment, the processing structure is configured, in the event that a session defines a sequence of two or more exercises, to cause distribution of new electrical stimulation signals sequentially in accordance with the sequence.

In an embodiment, the processor-readable storage medium stores digital exertion data for a plurality of muscle groups.

In an embodiment, the exertion data stored in association with each of the at least one muscle group is also stored in association with an identification of a respective output path of the signal distributor, wherein the processing structure is configured to cause the signal distributor to convey new electrical stimulation signals in accordance with the associated respective output path.

In an embodiment, each digital exertion data comprises a sequence of intensity values derived from the one or more electrical signals captured during the exertion regime, wherein the signal generator generates a sequence of voltage values for the new electrical stimulation signals based on the intensity values.

In an embodiment, the digital exertion data comprises high and low intensity values and rate values derived from the one or more electrical signals captured during the exertion regime.

In an embodiment, the processing structure is configured to cause the signal generator to generate new biphasic electrical stimulation signals based on the digital exertion data.

In accordance with another aspect of the invention, there is provided a processor-implemented method of stimulating one or more muscle groups, the method comprising: storing, in association with each of at least one muscle group, digital exertion data representative of one or more action potentials captured during an exertion regime from the muscle group of a respective subject; automatically retrieving the digital exertion data; automatically generating new electrical stimulation signals based on the digital exertion data; and conveying the new electrical stimulation signals to one or more respective muscle groups of at least one different subject thereby to electrically stimulate the one or more muscle groups.

In an embodiment, the method comprises storing one or more exercises each defining the time stamped digital exertion data for one or more muscle groups.

In an embodiment, the method comprises in the event that an exercise defines digital exertion data for two or more muscle groups, simultaneously distributing new electrical stimulation signals based on the digital exertion data for the two or more muscle groups.

In an embodiment, the method comprises storing one or more sessions each defining one or more of the exercises.

In an embodiment, the method comprises in the event that a session defines a sequence of two or more exercises, distributing new electrical stimulation signals sequentially in accordance with the sequence.

In an embodiment, the method comprises storing digital exertion data for a plurality of muscle groups.

In an embodiment, the method comprises storing the exertion data stored in association with each of the at least one muscle group also in association with an identification of a respective output path, wherein the conveying comprises conveying new electrical stimulation signals in accordance with the associated respective output path.

In an embodiment, each digital exertion data comprises a sequence of intensity values derived from the one or more electrical signals captured during the exertion regime, wherein the generating comprises generating a sequence of voltage values for the new electrical stimulation signals based on the intensity values.

In an embodiment, each digital exertion data comprises high and low intensity values and rate values derived from the one of more electrical signals captured during the exertion regime.

In an embodiment, the generating comprises generating new biphasic electrical stimulation signals based on the digital exertion data.

In accordance with another aspect of the invention, there is provided a non-transitory computer readable medium embodying a computer program executable on a computing system for stimulating one or more muscle groups, the computer program comprising computer program code for storing, in association with each of at least one muscle group, digital exertion data representative of one or more electrical signals captured during an exertion regime from the muscle group of a respective subject; computer program code for retrieving the digital exertion data; computer program code for generating new electrical stimulation signals based on the digital exertion data; and computer program code for conveying the new electrical stimulation signals to one or more respective muscle groups of at least one different subject thereby to electrically stimulate the one or more muscle groups.

In accordance with another aspect of the invention, there is provided a system for providing exercise session data comprising: a capture subsystem capturing one or more action potentials from at least one muscle group of a subject during an exertion regime, the capture subsystem comprising: a processor-readable storage medium; processing structure generating digital exertion data representative of the one or more action potentials and creating the exercise session data by: storing the digital exertion data in association with an identification of the respective muscle group in the processor-readable storage medium; storing, in the processor-readable storage medium, one or more exercises each defining at least the digital exertion data for one or more muscle groups; and storing, in the processor-readable storage medium, one or more sessions each defining at least one or more of the exercises, the system further comprising a publishing subsystem for publishing the exercise session data for download and use by at least one different subject to cause another processing structure to generate and distribute new electrical stimulation signals to one or more respective muscle groups of the at least one different subject.

In accordance with another aspect of the invention, there is provided a method of providing exercise session data comprising capturing one or more action potentials from at least one muscle group of a subject during an exertion regime; generating, using a processing structure, digital exertion data representative of the one or more action potentials; and creating the exercise session data by: storing the digital exertion data in association with an identification of the respective muscle group in a processor-readable storage medium; storing, in the processor-readable storage medium, one or more exercises each defining at least the digital exertion data for one or more muscle groups; and storing, in the processor-readable storage medium, one or more sessions each defining at least one or more of the exercises; the method further comprising publishing the exercise session data for download and use by at least one different subject to cause another processing structure generate and distribute new electrical stimulation signals to one or more respective muscle groups of the at least one different subject.

In accordance with another aspect of the invention, there is provided a non-transitory computer readable medium embodying a computer program executable on a computing system for providing exercise session data, the computer program comprising computer program code for capturing one or more action potentials from at least one muscle group of a subject during an exertion regime; computer program code for generating, using a processing structure, digital exertion data representative of the one or more action potentials; and computer program code for creating the exercise session data by: storing the digital exertion data in association with an identification of the respective muscle group in a processor-readable storage medium; storing, in the processor-readable storage medium, one or more exercises each defining at least the digital exertion data for one or more muscle groups; and storing, in the processor-readable storage medium, one or more sessions each defining at least one or more of the exercises; the computer program further comprising computer program code for publishing the exercise session data for download and use by at least one different subject to cause another processing structure generate and distribute new electrical.

Other aspects and advantages will be apparent from the following description and from the drawings.

BRIEF DESCRIPTION OF THE DRAWINGS

Embodiments of the invention will now be described with reference to the appended drawings in which:

FIG. 8 is a table containing digital exertion data associated with output path data.

DETAILED DESCRIPTION

Figure 1:
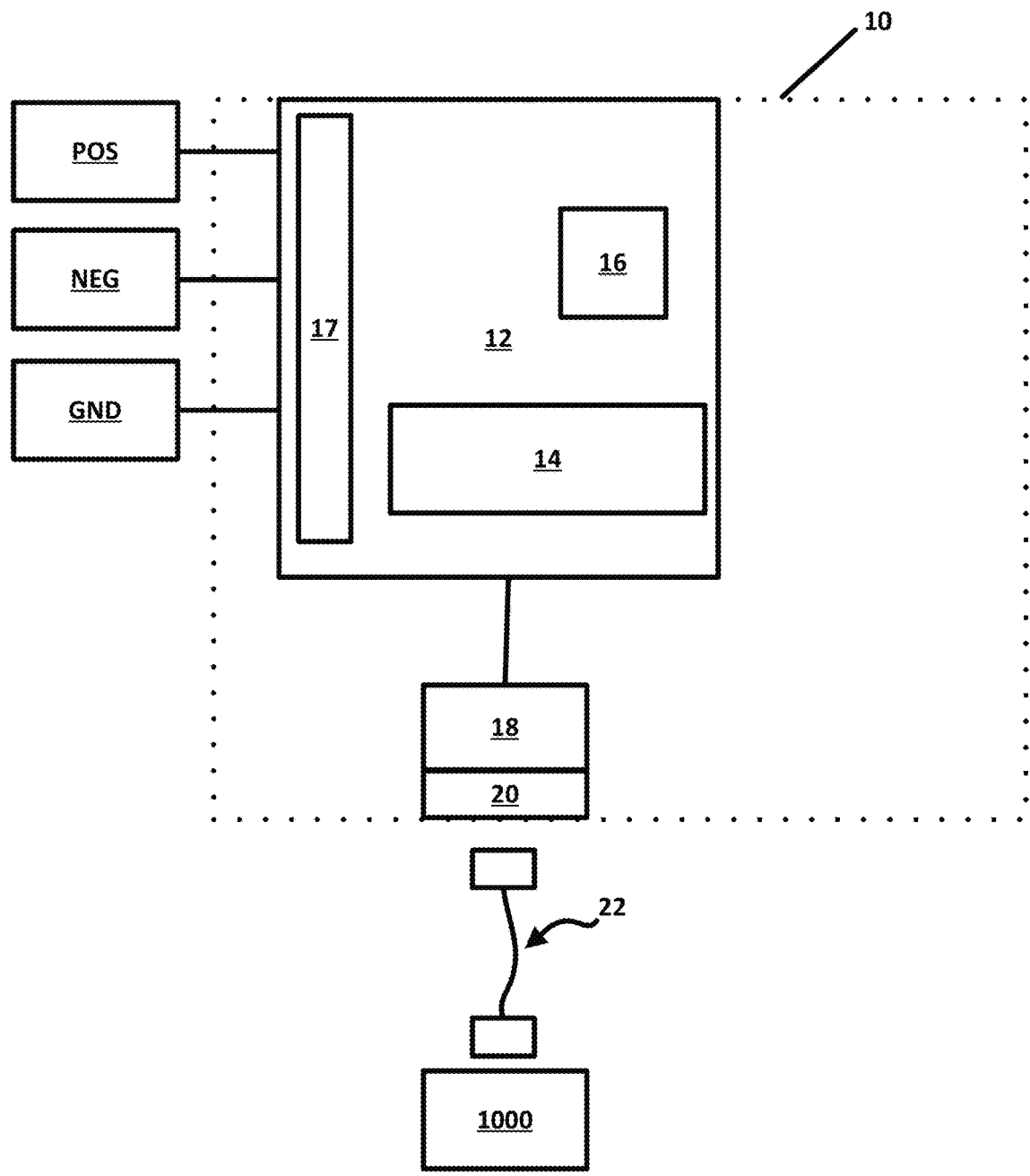
FIG. 1 is a schematic block diagram of a system for providing exercise session data including a capture subsystem and a controller, according to an embodiment.

FIG. 1 is a schematic block diagram of a system for providing exercise session data including a capture subsystem 10 and a controller 1000, according to an embodiment. In this embodiment, capture subsystem 10 is powered by, and is in data communications with, controller 1000 via a USB (Universal Serial Bus) connection 22. The power received by capture subsystem 10 from controller 1000 powers a main board 12, in this embodiment an Arduino™ Uno embedded microprocessor board, which in turn converts the voltage levels if required to that required of various components including a processing structure which is, in this embodiment, a single central Atmel ATMega328 processor 14. Central processor 14 is further in communications with processor-readable memory 16 via an internal bus.

Central processor 14 is also connected to USB hub 18, which is in turn connected to USB interface 20. USB interface 20 can receive an external USB cable 22 for conveying power and data communications with controller 1000 via one of its own USB ports in its communications interface 1020 such that the components of capture subsystem 10 may be operated by controller 1000 or may at least receive data captured and/or produced by capture subsystem 10 as will be described. A simple user interface, including buttons and a dot matrix display (not shown) are also in communications with the processing structure 14 and accessible to a user for operation of capture subsystem 10.

In this embodiment, main board 12 also supports electrical connections to three electrical probes: POS, NEG and GND, via a sampling chip 17 for capturing one or more action potentials from at least one muscle group of a subject during an exercise regime. The processing structure produces exertion data based on the captured one or more action potentials, as will be described.

Figure 2:
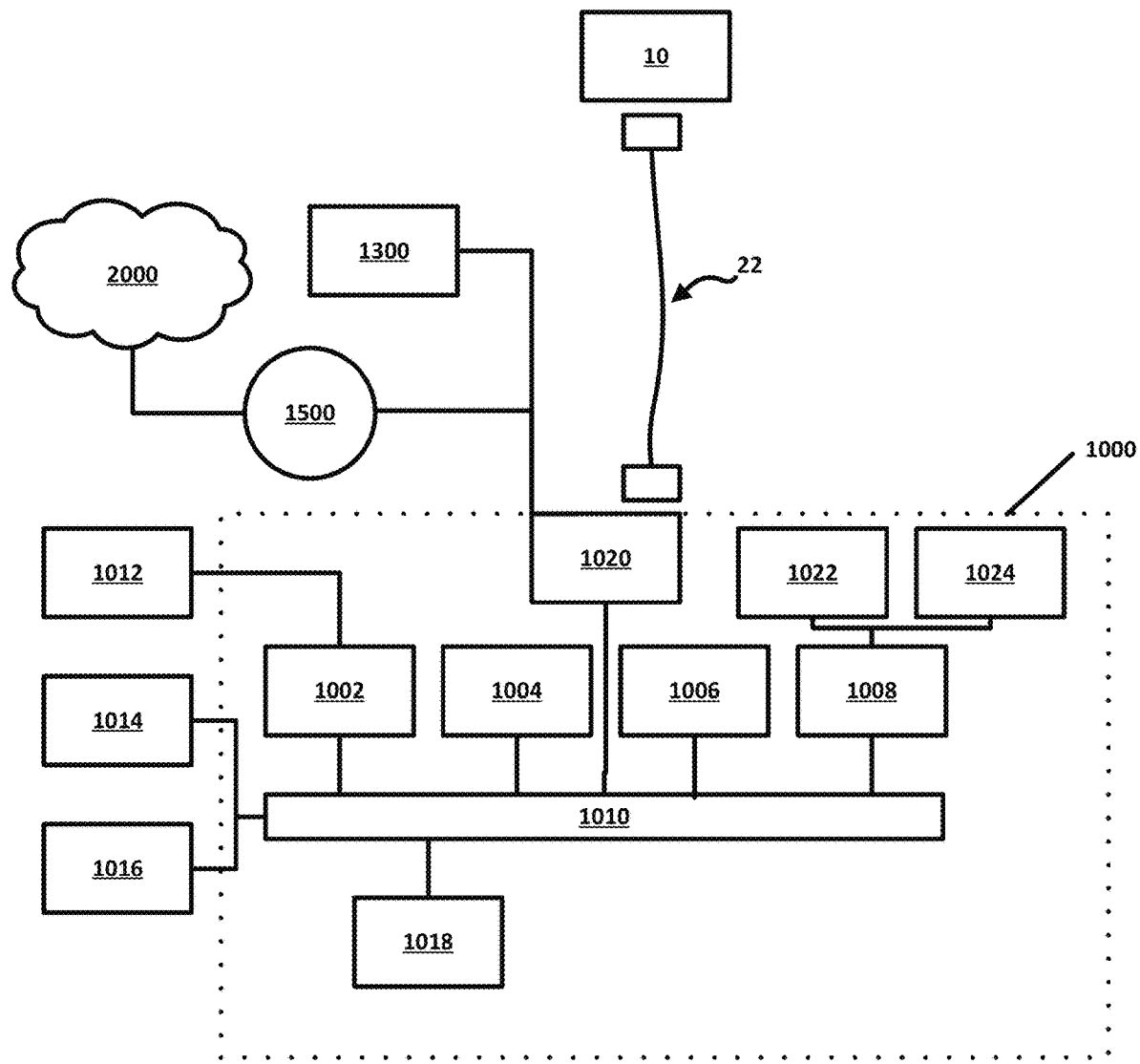
FIG. 2 is a schematic block diagram of the system of FIG. 1 with the controller shown in further detail, according to an embodiment.

FIG. 2 is a schematic block diagram of the system of FIG. 1 with the controller 1000 shown in further detail, according to an embodiment. In this embodiment, controller 1000 is a computing system that is incorporated into a laptop or desktop computer or other similar device.

Controller 1000 includes a bus 1010 or other communication mechanism for communicating information, and a processor 1018 coupled with the bus 1010 for processing the information. Controller 1000 also includes a main memory 1004, such as a random access memory (RAM) or other dynamic storage device (e.g., dynamic RAM (DRAM), static RAM (SRAM), and synchronous DRAM (SDRAM)), coupled to the bus 1010 for storing information and instructions to be executed by processor 1018. In addition, the main memory 1004 may be used for storing temporary variables or other intermediate information during the execution of instructions by the processor 1018. Processor 1018 may include memory structures such as registers for storing such temporary variables or other intermediate information during execution of instructions. The controller 1000 further includes a read only memory (ROM) 1006 or other static storage device (e.g., programmable ROM (PROM), erasable PROM (EPROM), and electrically erasable PROM (EEPROM)) coupled to the bus 1010 for storing static information and instructions for the processor 1018.

The controller 1000 also includes a disk controller 1008 coupled to the bus 1010 to control one or more storage devices for storing information and instructions, such as a magnetic hard disk 1022, and a removable media drive 1024 (e.g., floppy disk drive, read-only compact disc drive, read/write compact disc drive, compact disc jukebox, tape drive, and removable magneto-optical drive). The storage devices may be added to the controller 1000 using an appropriate device interface (e.g., small computing system interface (SCSI), integrated device electronics (IDE), enhanced-IDE (E-IDE), direct memory access (DMA), or ultra-DMA).

The controller 1000 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The controller 1000 may also include a display controller 1002 coupled to the bus 1010 to control a display 1012, such as a liquid crystal display (LCD) screen, for displaying information to a user of the controller 1000. The controller 1000 includes input devices, such as a keyboard 1014 and a pointing device 1016, for interacting with a computer user and providing information to the processor 1018. The pointing device 1016, for example, may be a mouse, a trackball, or a pointing stick for communicating direction information and command selections to the processor 1018 and for controlling cursor movement on the display 1012. In addition, a printer may provide printed listings of data stored and/or generated by the controller 1000.

In this embodiment, the controller 1000 performs a portion or all of the processing steps of the invention in response to the processor 1018 executing one or more sequences of one or more instructions contained in a memory, such as the main memory 1004. Such instructions may be read into the main memory 1004 from another computer readable medium, such as a hard disk 1022 or a removable media drive 1024. One or more processors in a multi-processing arrangement may also be employed to execute the sequences of instructions contained in main memory 1004. In alternative embodiments, hard-wired circuitry may be used in place of or in combination with software instructions. Thus, embodiments are not limited to any specific combination of hardware circuitry and software.

As stated above, the controller 1000 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the controller 1000, for driving a device or devices for implementing aspects of the invention, and for enabling the controller 1000 to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

In this embodiment, the applications software includes an application and corresponding database structured for retrieving, editing (such as smoothing or adjusting levels) and visualizing exertion datasets, and for organizing exertion datasets into exercises session datasets as will be described. The application preferably also permits live playback of a stored exercise session dataset through to a stimulation subsystem such as will be described below, or uploaded for storage to a device that incorporates a stimulation subsystem as well as an internal processor-readable memory capable of storing one or more exercise session datasets.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

A computer readable medium providing instructions to a processor 1018 may take many forms, including but not limited to, non-volatile media, volatile media, and transmission media. Non-volatile media includes, for example, optical, magnetic disks, and magneto-optical disks, such as the hard disk 1022 or the removable media drive 1024. Volatile media includes dynamic memory, such as the main memory 1004. Transmission media includes coaxial cables, copper wire and fiber optics, including the wires that make up the bus 1010. Transmission media also may also take the form of acoustic or light waves, such as those generated during radio wave and infrared data communications.

Various forms of computer readable media may be involved in carrying out one or more sequences of one or more instructions to processor 1018 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the controller 1000 may receive the data on the telephone line and use an infrared transmitter to convert the data to an infrared signal. An infrared detector coupled to the bus 1010 can receive the data carried in the infrared signal and place the data on the bus 1010. The bus 1010 carries the data to the main memory 1004, from which the processor 1018 retrieves and executes the instructions. The instructions received by the main memory 1004 may optionally be stored on storage device 1022 or 1024 either before or after execution by processor 1018.

The controller 1000 also includes a communication interface 1020 coupled to the bus 1010. The communication interface 1020 provides a two-way data communication coupling to a network link that is connected to, for example, a local area network (LAN) 1500, or to another communications network 2000 such as the Internet, or to another device via, for example, a USB connection such as device 10. The communication interface 1020 may include a network interface card to attach to any packet switched LAN. As another example, the communication interface 1020 may include an asymmetrical digital subscriber line (ADSL) card, an integrated services digital network (ISDN) card or a modem to provide a data communication connection to a corresponding type of communications line. Wireless links may also be implemented. In any such implementation, the communication interface 1020 sends and receives electrical, electromagnetic or optical signals that carry digital data streams representing various types of information and, in the case of USB, electrical power.

The network link typically provides data communication through one or more networks to other data devices. For example, the network link may provide a connection to another computer through a local network 1500 (e.g., a LAN) or through equipment operated by a service provider, which provides communication services through a communications network 2000. The local network 1500 and the communications network 2000 use, for example, electrical, electromagnetic, or optical signals that carry digital data streams, and the associated physical layer (e.g., CAT 5 cable, coaxial cable, optical fiber, etc). The signals through the various networks and the signals on the network link and through the communication interface 1020, which carry the digital data to and from the controller 1000 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The controller 1000 can transmit and receive data, including program code, through the network(s) 1500 and 2000, the network link and the communication interface 1020. Moreover, the network link may provide a connection through a LAN 1500 to a mobile device 1300 such as a personal digital assistant (PDA) laptop computer, or cellular telephone.

Figure 3:
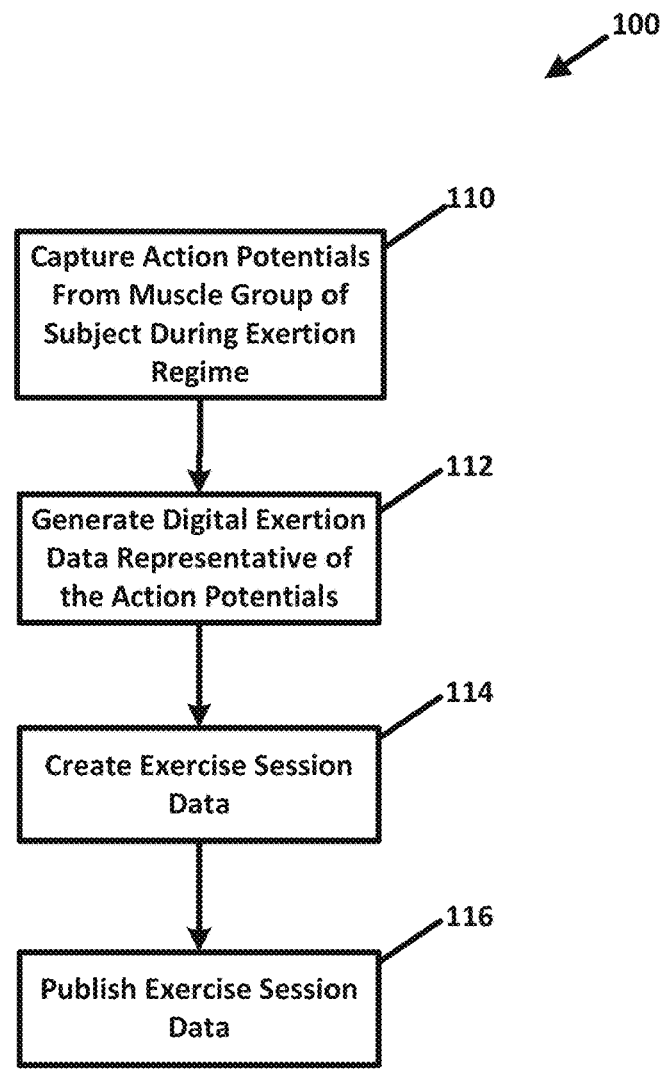
FIG. 3 is a flowchart depicting the general steps in a method of providing exercise session data, according to an embodiment.

FIG. 3 is a flowchart depicting the general steps in a method 100 of providing exercise session data, according to an embodiment. Capture subsystem 10 is controlled by controller 1000 to cause capture subsystem 10 to capture, using probes POS, NEG and GND, one or more action potentials from at least one muscle group of a subject during an exertion regime, and to generate digital exertion data representative of the action potentials. The digital exertion data is stored temporarily by capture subsystem 10 but is transferred via USB connection 22 for storage by controller 1000 in association with an identification of the corresponding muscle group, as will be described.

As used herein, a muscle group is a term referring broadly to a distinct muscle area—such as the left pectoral muscles or the upper abdominal muscles—as opposed to, for example, any individual muscle fiber.

In an embodiment, for capture of action potentials covering a broad range of potential output situations, multiple subjects are probed. First, the subjects are divided into groups based on their body fat content, as differences in body fat content have significant impacts on the signal levels of action potentials being captured from muscles, as well as on EMS itself. The subjects in each group those within about 2% of body fat composition of each other—are then further subdivided into three strength subgroups: strong, intermediate, and weak. The subjects in each subgroup are then probed so that action potentials may be captured during various exertion regimes. This involves attaching the POS, NEG and GND probes, preferably with an appropriate conductive pad and conductive gel, to multiple muscle groups of each subject so that, during a respective exertion regime, action potentials for the respective muscle groups can be captured. The subject is then subjected to a very specific training programme so that action potentials can be captured for every repetition from each muscle group during an exertion regime (step 110). Based on the captured action potentials, digital exertion data is generated that is representative of the action potentials (step 112) and is stored in association with an identification of the corresponding muscle group. In this embodiment, the digital exertion data is also stored in processor-readable memory in association with data corresponding to an output path on which a signal distributor (to be described) of an EMS delivery device would convey a new electrical stimulation signal based on the exertion data, as shown in FIG. 8. In this embodiment, the digital exertion data is generated by first digitally sampling the action potential waveforms captured from a muscle group during repetitions of a particular exercise, such as from the front shoulder muscle group during 15 repetitions of a shoulder raise exercise (see Stim4 in FIG. 8). One set or multiple—for example 3 or 4 sets of repetitions may be captured in the exertion dataset. The exercises are done at a controlled pace, which in this embodiment is 4 seconds negative and 2 seconds positive as defined by CanFitPro as the optimal time under tension for foundation level clients. In other embodiments different times under tension may be appropriate. In this embodiment, the optimal weight per exercise is approximately 60 to 70% of a subject's maximum strength (which is defined by CanFitPro as optimal foundation level weight and length of exercise).

In this embodiment, each digital exertion dataset comprises a sequence of time-stamped intensity values derived from the one or more action potentials captured during the exertion regime, so that subsequent generating of new electrical stimulation signals can include generating a sequence of voltage values for the new electrical stimulation signals based on the intensity values. In other embodiments, however, the digital exertion data may be stored in other ways for efficiency or ease of handling, such as in the form similar to that in which audio data may be stored, including compressed audio data. For example, the digital exertion data may alternatively include just high and low intensity values for the action potentials captured during the given exertion regime, and rate values for oscillating between the high and low intensity values over a time period, or a derived formula for the action potentials of the muscle group over a time period.

While embodiments are contemplated in which just a single exertion dataset is captured from a single muscle group of a subject, in this embodiment multiple exertion datasets are captured from multiple muscle groups and can be grouped into exercises and sessions to create exercise session data (step 114). Such grouping may be done manually or may be done using applications software running on controller 1000 according to an automated or partly-automated script for capturing action potentials from subjects.

For example, protagonist and antagonist muscles (such as biceps as protagonist and triceps as antagonist for a bicep curl exercise, or triceps as protagonist and biceps as antagonist for a tricep extension exercise) might be grouped together under a single exercise so that invocation of the new electrical stimulation signals according to the exercise can involve simultaneous distribution of the new electrical signals to the two or more different muscle groups thereby to more accurately reproduce the effects of the exercise. Table 1 below shows, for example, an Upper Back exercise identified as Ex1, that is a group of exertion datasets Stim1, Stim2 and Stim 3 to be used to generate and simultaneously distribute new electrical stimulation signals via respective output paths. Additional columns may be provided for additional exertion datasets to be so grouped together. Table 1 also shows columns for repeats in the event that multiple sets of exercises are to be played back when outputting the new electrical stimulation signals. For example, a Lower Back exercise identified as Ex2 and implicating exertion datasets corresponding to Stim5, Stim8 and Stim10 is defined for generating new electrical stimulation signals that will repeat 4 times with a pause of 20 seconds in between repeats.

TABLE 1

| Exercise ID | Exercise Name | Stim A | Stim B | Stim C | Repeated | Pause |
|---|---|---|---|---|---|---|
| Ex1 | Upper Back | Stim1 | Stim2 | Stim3 | 3 | 20 s |
| Ex2 | Lower Back | Stim5 | Stim8 | Stim10 | 3 | 20 s |
| Ex3 | Upper Chest | Stim6 | Stim7 | — | 3 | 30 s |
| Ex4 | Front Abs | Stim9 | Stim10 | Stim5 | 4 | 30 s |
| Ex5 | Side Abs | Stim8 | n/a | n/a | 4 | 30 s |
| ... | ... | ... | ... | ... | ... | ... |

In this embodiment, an additional level of grouping is available in which exercises can be grouped into sessions, as shown in Table 2 below. With sessions, a sequence of exercises is defined such that the exercise are not to be outputted simultaneously (as are stimulations grouped into exercise as in Table 1) but in accordance with the specified sequence. Table 2 shows, for example, a Back and Chest session, identified as Sess1, that is defined as a group of exercises Ex1, Ex2 and Ex3. The individual exercises are to be done sequentially with a 60 second pause in between each of exercises Ex1, Ex2 and Ex3. It will be noted that during playback of a given exercise, any individual stimulations grouped such as is shown in FIG. 8 under the given exercise are still to be outputted simultaneously as described above. It is preferred that an exercise sequence for a session be sequenced for progressively declining workload such that the lowest workload exercise in the session is invoked last during playback.

TABLE 2

| Session ID | Session Name | Exercise Sequence | Pause Between Exercise |
|---|---|---|---|
| Sess1 | Back and Chest | Ex1, Ex2, Ex3 | 60 s |
| Sess2 | Abs | Ex4, Ex5 | 60 s |
| Sess3 | Legs | ... | ... |
| ... | ... | ... | ... |

In this embodiment, with the exercise session data having been created at step 114, the exercise session data may be published (step 116) for use by others. This may be done using software running on controller 1000 that interfaces with an online social network or App Store to publish the exercise session data so that others can download the exercise session data either as an in-App purchase from a related App on a device, for free, or in some other format. In this sense, controller 1000 and the social network or App Store or other format constitute a publishing subsystem that enables the exercise session data to be downloaded and used by other people to cause another processing structure on devices owned or operated by the other people to generate and distribute the new electrical stimulation signals to one or more respective muscle groups for themselves. In this way, embodiments herein enable the capture or "recording" of data indicative of muscle activity (i.e. action potentials) from a muscle group of one person and effectively the reverse process or "playback" of stimulation signals generated based on the captured data to a corresponding muscle group of one or potentially many other people. It may also be useful to employ embodiments of the system described herein to enable an individual to record action potentials for their muscles' exertion for potential later use by that exact same individual to help the individual to viscerally gauge whether they having improved their strength or endurance since their original recording, or to at least maintain a baseline for use by the individual, trainers or other personnel.

Figure 4:
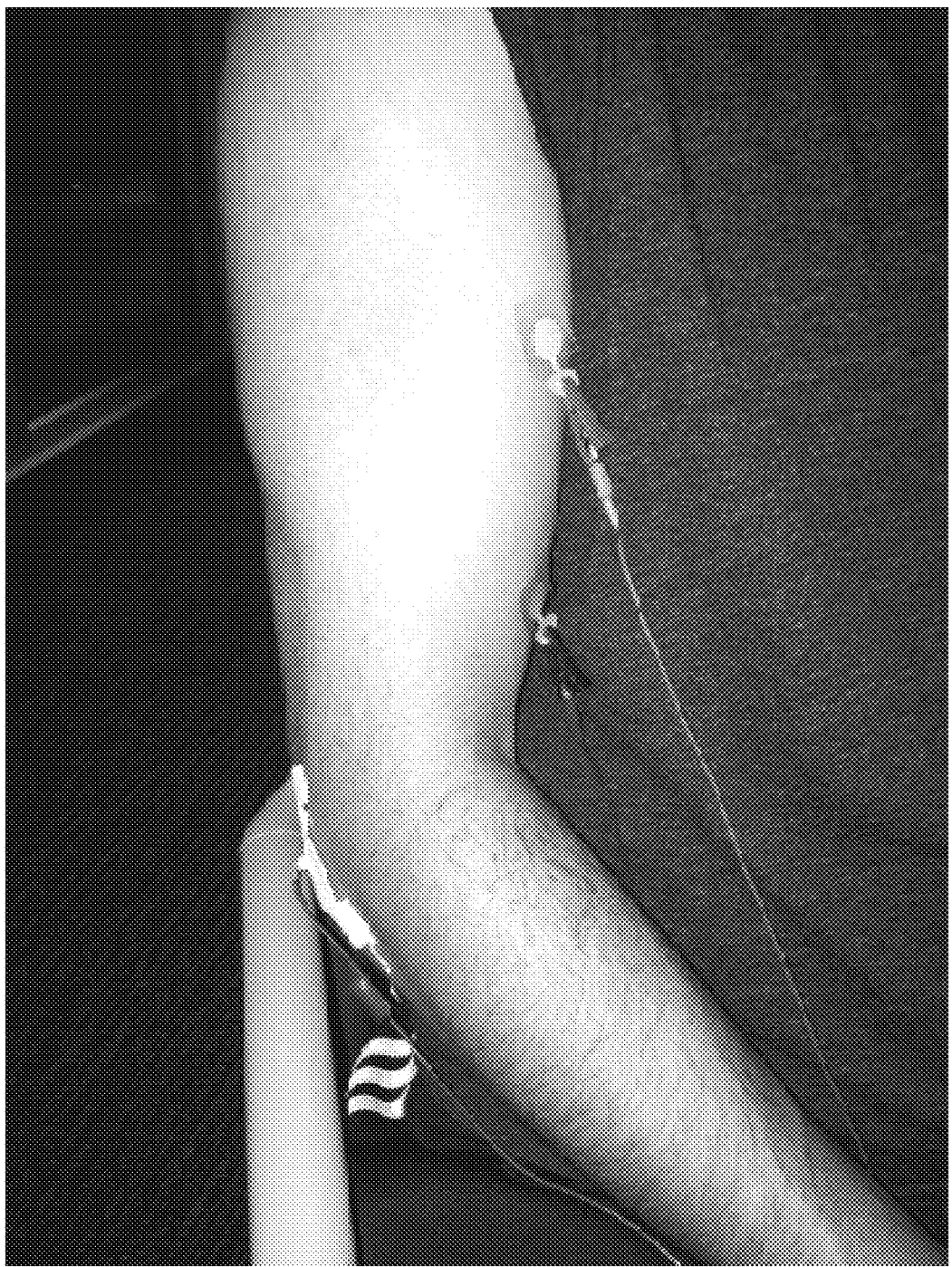
FIG. 4 is a diagram showing of electrical probes positioned on a subject's arm to receive and capture one or more electrical signals during an exercise regime.
Figure 5:
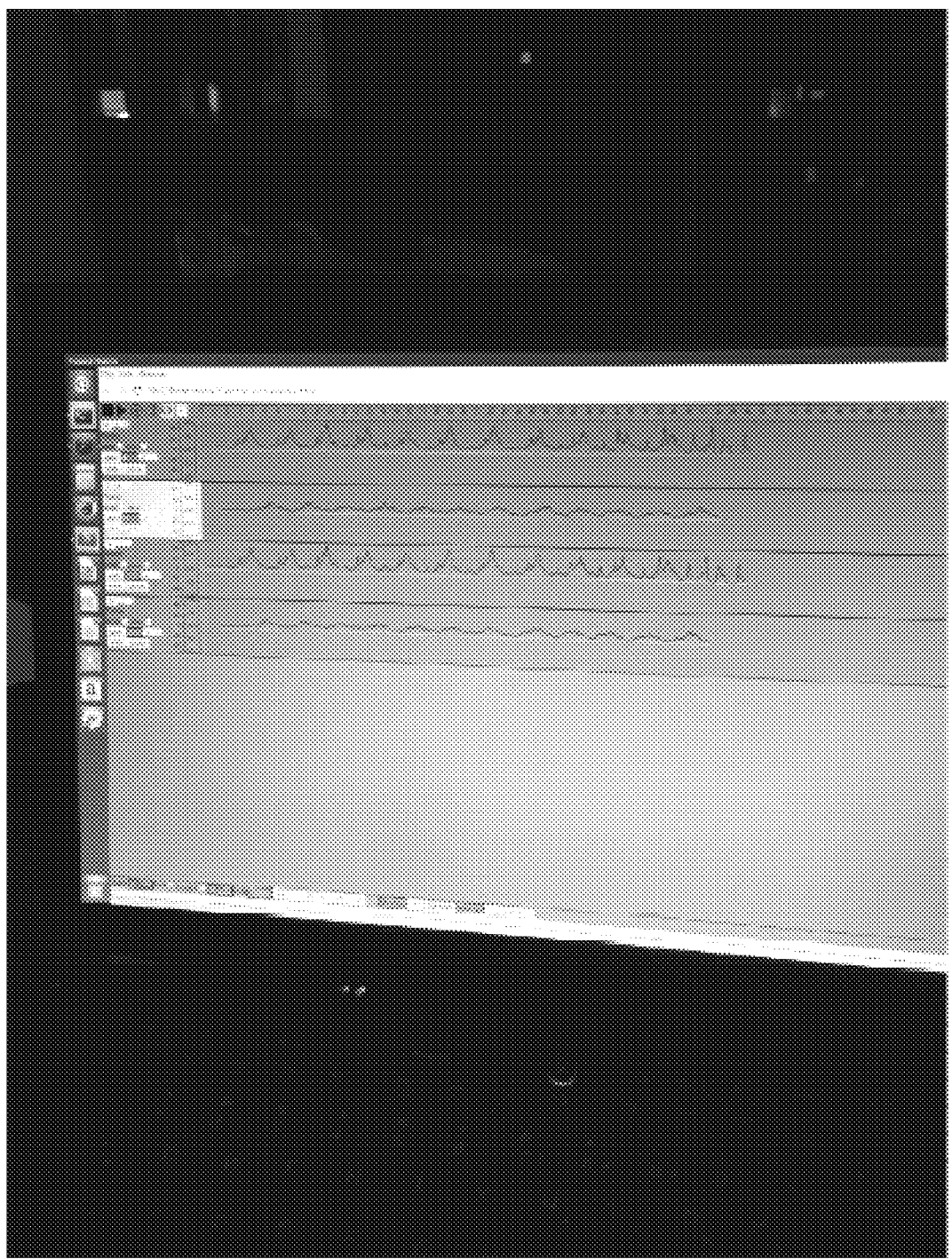
FIG. 5 is a diagram showing a display of the controller displaying visual representations of exertion data for respective ones of a number of muscle groups.

FIG. 4 is a diagram showing of electrical probes positioned on a subject's arm to receive and capture one or more action potentials during an exercise regime, according to an embodiment. FIG. 5 is a diagram showing a display of controller 1000 displaying visual representations of exertion data generated from the action potentials for respective ones of a number of muscle groups, according to an embodiment.

With the means by which exertion data is created and stored having been described, there will now be described how muscle groups may be stimulated based on the exertion data.

Figure 6:
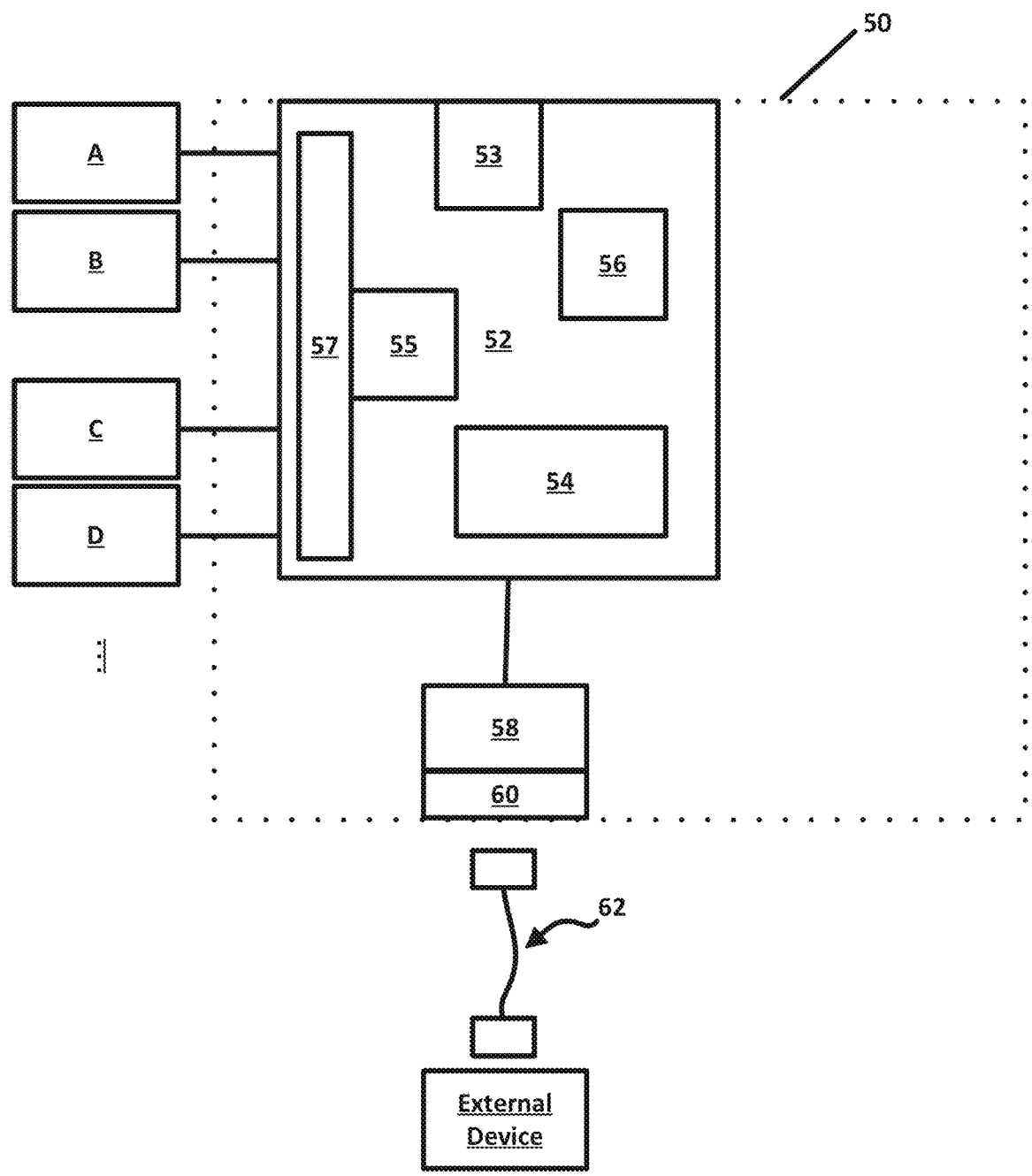
FIG. 6 is a schematic block diagram of a system for electrically stimulating multiple muscle groups, according to an embodiment.

FIG. 6 is a schematic block diagram of a system 50 for electrically stimulating multiple muscle groups, according to an embodiment. In this embodiment, system 50 is powered by a 12-Volt (V) internal battery 53, which provides power to a main board 52. Main board 52 can be in data communications with an external device such as a device similar to controller 1000 via a USB (Universal Serial Bus) connection 62. The power received from battery 53 powers a main board 12, in this embodiment an Arduino™ Uno embedded microprocessor board similar to that described above in connection with capture subsystem 10, which in turn converts the voltage levels if required to that required of various components including a processing structure which is, in this embodiment, a single central Atmel ATMega328 processor 54. Central processor 54 is further in communications with internal processor-readable memory 56 via an internal bus.

Central processor 54 is also connected to USB hub 58, which is in turn connected to USB interface 60. USB interface 60 can receive an external USB cable 62 for enabling data communications (and, in other embodiments, charging or other power communications) with the external device via one of its own USB ports such that system 50 can download exercise session data including digital exertion data that can be retrieved by system 50 and used to cause a signal generator 55 to generate new electrical stimulation signals accordingly. In this embodiment, signal generator 55 includes an 80-channel digital-to-analog converter (DAC) having a 5V/10 bit rating. The DAC may be operated with 40-channels if both positive and negative voltage outputs are required for each output lead. A simple user interface, including buttons and a dot matrix display (not shown) are also in communications with the processing structure 54 and accessible to a user for operation of system 50. In this embodiment, main board 52 also supports electrical connections to several electrical probes (only probe pairs A-B and C-D are shown for ease of understanding, but many more to cover various muscle groups would be available in this embodiment) for conveying new electrical stimulation signals to respective muscle groups of at least one subject as directed by a signal distributor 55 under control of processing structure 55, for distributing the new electrical stimulation signals as will be described.

In an embodiment, system 50 is in a suit format, with the suit holding the probes in predefined and fixed locations with respect to a muscle group of the user rather than requiring the user to manually place probes in association with the multiple muscle groups. In this way, the user can wear the suit and can trigger generation and distribution of the new electrical stimulation signals to respective probe locations associated with respective muscle groups. In an embodiment, the suit is constructed of a combination of Lycra, electrolycra, polyester posture brace, wiring, buttons, and semi conducting gel.

Portions of system 50 may be treated as a stimulation subsystem, with system 50 being used as a standalone/portable EMS delivery product, for example its internal processor-readable memory 56 being loaded with and storing the exercise session data including exertion data to be used to generate new electrical stimulation signals. Alternatively, the stimulation subsystem components (the processing structure 54, the signal generator 55 and the signal distributor 57) can operate in a manner such that the exercise session data including the exertion data is received from some external processor-readable memory, such as that provided on a device such as controller 1000 or that accessed via controller 1000, that can be transmitted through the USB cable 62 or via other means to be used by the stimulation subsystem to generate and distribute the new electrical stimulation signals accordingly.

Figure 7:
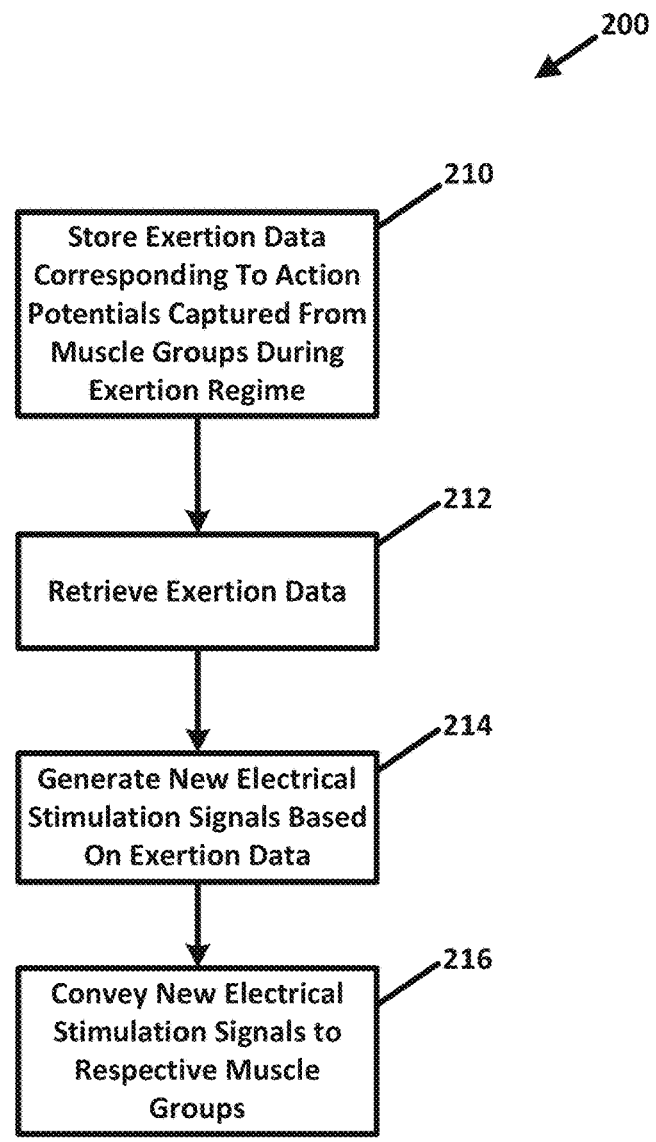
FIG. 7 is a flowchart depicting the general steps in a method of stimulating one or more muscle groups, according to an embodiment.

FIG. 7 is a flowchart depicting the general steps for a processor-implemented method 200 of stimulating one or more muscle groups, according to an embodiment. A system such as system 50 stores the exertion data in the form of exercise session data as described above in connection with FIG. 8 and Tables 1 and 2, in processor-readable storage medium 56 (step 210). As described above, the exertion data of the exercise session data is representative of one or more action potentials captured during an exertion regime from the muscle group of a respective subject. It is not required, nor is it very likely, that the person operating device 50 to receive electrical stimulation signals will be the same subject from which the exertion data was captured. Such exercise session data may be kept stored in processor-readable storage medium 56 until such time as a user is ready to use it. When a user is ready to use it, the exertion data in the exercise session is retrieved (212) and is used by processing structure 54 and signal generator 55 to generate new electrical stimulation signals based on the exertion data (step 214). In this embodiment, signal generator 55 comprises a digital to analog converter and, depending on the voltage levels on main board 52 of device 50, an amplifier for amplifying the resultant analog signals to be suitable for conveyance to a muscle group of a user. With the new electrical stimulation signals having been generated based on the exertion data at step 214, the new electrical stimulation signals are conveyed to respective muscle groups via respective probes in accordance with the output path associated with the individual exertion datasets (See Table 1 FIG. 8).

In this embodiment, the signal generator 55 generates new biphasic electrical stimulation signals based on the digital exertion data. A constant current source with a tailored step response is used. The current source is achieved by a combination of a voltage amplifier and PID (proportional-integral-derivative) feedback loop. The poles of this feedback loop are selected to minimize overshoot and maximize settling time of its step response. The non-settling manner of the stimulation signal has been found to provide improved muscle contraction as compared to a steady current. The constant current generator allows for a more accurate measure of charge flow through the skin, allowing for decreased discomfort arising from charge build up. Frequency, pulse width, and pulse pause (time between negative and positive pulses) are all software-adjustable to ensure maximum muscle activation on an individual muscle basis.

In this embodiment, prior to stimulating the user's muscle groups based the exercise session data, warmup electrical stimulation signals may be conveyed to the muscle groups of the user.

Although embodiments have been described with reference to the drawings, those of skill in the art will appreciate that variations and modifications may be made without departing from the spirit, scope and purpose of the invention as defined by the appended claims.

For example, while embodiments described herein include a system for electrically stimulating one or more muscle groups with a stimulation subsystem based on an Arduino™ Uno ATMega328, other configurations, such as for example those based on other devices provided by Arduino™, or the Intel Edison™, Raspberry Pi™, and Intel Galileo™ systems, may be configured to function as described herein.

What is claimed is:

1. A system for electrically stimulating one or more muscle groups comprising:
   a processor-readable storage medium storing, in association with each of at least one muscle group, digital exertion data representative of one or more action potentials captured during an exertion regime from the muscle group of a respective subject;
   a signal generator for generating electrical stimulation signals;
   processing structure configured to automatically retrieve digital exertion data from the processor-readable storage medium and to automatically cause the signal generator to generate new electrical stimulation signals based on the digital exertion data;
   a signal distributor for conveying the new electrical stimulation signals from the signal generator to one or more respective muscle groups of at least one different subject;
   a capture subsystem capturing one or more action potentials from at least one muscle group of a subject during an exertion regime, the capture subsystem comprising:
   a processor-readable storage medium;
   processing structure generating digital exertion data representative of the one or more action potentials and creating the exercise session data by:
   storing the digital exertion data in association with an identification of the respective muscle group in the processor-readable storage medium;
   storing, in the processor-readable storage medium, one or more exercises each defining at least the digital exertion data for one or more muscle groups; and
   storing, in the processor-readable storage medium, one or more sessions each defining at least one or more of the exercises, a publishing subsystem for publishing the exercise session data for download and use by at least one different subject to cause another processing structure to generate and distribute new electrical stimulation signals to one or more respective muscle groups of the at least one different subject.

2. The system of claim 1, wherein the processing structure is configured to retrieve the digital exertion data from the processor-readable storage medium as one or more exercises each defining the digital exertion data for one or more muscle groups.

3. The system of claim 2, wherein the processing structure is configured, in the event that an exercise defines digital exertion data for two or more muscle groups, to cause simultaneous distribution of new electrical stimulation signals based on the digital exertion data for the two or more muscle groups.

4. The system of claim 2, wherein the processing structure is configured to retrieve the digital exertion data from the processor-readable storage medium as one or more sessions each defining one or more of the exercises.

5. The system of claim 4, wherein the processing structure is configured, in the event that a session defines a sequence of two or more exercises, to cause distribution of new electrical stimulation signals sequentially in accordance with the sequence.

6. The system of claim 1, wherein the processor-readable storage medium stores digital exertion data for a plurality of muscle groups, and wherein the exertion data stored in association with each of the at least one muscle group is also stored in association with an identification of a respective output path of the signal distributor, wherein the processing structure is configured to cause the signal distributor to convey new electrical stimulation signals in accordance with the associated respective output path.

7. The system of claim 1, wherein each digital exertion data comprises a sequence of intensity values derived from the one or more action potentials captured during the exertion regime, wherein the signal generator generates a sequence of voltage values for the new electrical stimulation signals based on the intensity values.

8. The system of claim 1, wherein the digital exertion data comprises high and low intensity values and rate values derived from the one of more action potentials captured during the exertion regime.

9. The system of claim 1, wherein the processing structure is configured to cause the signal generator to generate new biphasic electrical stimulation signals based on the digital exertion data.

10. A processor-implemented method of stimulating one or more muscle groups, the method comprising:

storing, in association with each of at least one muscle group, digital exertion data representative of one or more action potentials captured during an exertion regime from the muscle group of a respective subject;

automatically retrieving the digital exertion data;

automatically generating new electrical stimulation signals based on the digital exertion data;

conveying the new electrical stimulation signals to one or more respective muscle groups of at least one different subject thereby to electrically stimulate the one or more muscle groups;

capturing one or more action potentials from at least one muscle group of a subject during an exertion regime;

generating, using a processing structure, digital exertion data representative of the one or more action potentials; and creating the exercise session data by:
  storing the digital exertion data in association with an identification of the respective muscle group in a processor-readable storage medium;
  storing, in the processor-readable storage medium, one or more exercises each defining at least the digital exertion data for one or more muscle groups; and
  storing, in the processor-readable storage medium, one or more sessions each defining at least one or more of the exercises; and
  publishing the exercise session data for download and use by at least one different subject to cause another processing structure generate and distribute new electrical stimulation signals to one or more respective muscle groups of the at least one different subject.

11. The processor-implemented method of claim 10, comprising:
  storing one or more exercises each defining the digital exertion data for one or more muscle groups, and in the event that an exercise defines digital exertion data for two or more muscle groups, simultaneously distributing new electrical stimulation signals based on the digital exertion data for the two or more muscle groups.

12. The processor-implemented method claim 10, comprising:
  storing one or more sessions each defining one or more of the exercises.

13. The processor-implemented method of claim 12, comprising: in the event that a session defines a sequence of two or more exercises, distributing new electrical stimulation signals sequentially in accordance with the sequence.

14. The processor-implemented method of claim 10, comprising: storing digital exertion data for a plurality of muscle groups, and storing the exertion data stored in association with each of the at least one muscle group also in association with an identification of a respective output path, wherein the conveying comprises conveying new electrical stimulation signals in accordance with the associated respective output path.

15. The processor-implemented method of claim 10, wherein each digital exertion data comprises a sequence of intensity values derived from the one or more action potentials captured during the exertion regime, wherein the generating comprises generating a sequence of voltage values for the new electrical stimulation signals based on the intensity values, and wherein each digital exertion data comprises high and low intensity values and rate values derived from the one of more action potentials captured during the exertion regime.

16. The processor-implemented method of claim 10, wherein the generating comprises generating new biphasic electrical stimulation signals based on the digital exertion data.

17. A non-transitory computer readable medium embodying a computer program executable on a computing system for stimulating one or more muscle groups, the computer program comprising:
  computer program code for storing, in association with each of at least one muscle group, digital exertion data representative of one or more action potentials captured during an exertion regime from the muscle group of a respective subject;
  computer program code for retrieving the digital exertion data;
  computer program code for generating new electrical stimulation signals based on the digital exertion data;
  computer program code for conveying the new electrical stimulation signals to one or more respective muscle groups of at least one different subject thereby to electrically stimulate the one or more muscle groups;

wherein the computer program further comprises:
  computer program code for capturing one or more action potentials from at least one muscle group of a subject during an exertion regime;
  computer program code for generating, using a processing structure, digital exertion data representative of the one or more action potentials; and
  computer program code for creating the exercise session data by:
    storing the digital exertion data in association with an identification of the respective muscle group in a processor-readable storage medium;
    storing, in the processor-readable storage medium, one or more exercises each defining at least the digital exertion data for one or more muscle groups; and
    storing, in the processor-readable storage medium, one or more sessions each defining at least one or more of the exercises; and
  computer program code for publishing the exercise session data for download and use by at least one different subject to cause another processing structure generate and distribute new electrical stimulation signals to one or more respective muscle groups of the at least one different subject.

* * * * *